United States Patent [19]

Hoffman

[11] Patent Number: 4,700,710

[45] Date of Patent: Oct. 20, 1987

[54] APERTURED ADHESIVELY APPLIED BODY ELECTRODE APPARATUS AND METHOD

[75] Inventor: Kent C. Hoffman, Cockeysville, Md.

[73] Assignee: Murray Electronics Associates Limited Partnership, Hunt Valley, Md.

[21] Appl. No.: 711,044

[22] Filed: Mar. 12, 1985

[51] Int. Cl.⁴ .............................................. A61B 5/04
[52] U.S. Cl. ................................... 128/641; 128/798; 128/802
[58] Field of Search ............... 128/783, 639, 640, 641, 128/643, 802, 803, 798

[56] References Cited

U.S. PATENT DOCUMENTS

| | | | |
|---|---|---|---|
| 2,555,037 | 5/1951 | Jensen | 128/803 |
| 2,872,926 | 11/1957 | Alderman | 128/640 |
| 3,387,608 | 6/1968 | Figar | 128/640 |
| 3,599,629 | 8/1971 | Gordy | 128/640 |
| 3,623,479 | 11/1971 | Day | 128/640 |
| 3,746,004 | 7/1973 | Jankelson | 128/803 |
| 3,848,600 | 11/1974 | Patrick Jr. et al. | 128/783 |
| 3,848,608 | 11/1974 | Leonard | 128/419 R |
| 3,972,329 | 8/1976 | Kaufman | 128/641 |
| 4,300,575 | 11/1981 | Wilson | 128/802 |
| 4,524,087 | 6/1985 | Engel | 128/639 |

*Primary Examiner*—Kyle L. Howell
*Assistant Examiner*—Randy Citrin
*Attorney, Agent, or Firm*—Nixon & Vanderhye

[57] ABSTRACT

An apertured flexible body electrode is first adhesively affixed to the external clean and dry body surface of a living subject. Thereafter, electrode gels or other preparations are inserted through the aperture(s) into the interface between the electrode and the subject's body surface. The apertures may thereafter be closed (e.g., with an adhesive-backed covering) to prevent subsequent leakage of the electrode gel or other preparation.

5 Claims, 13 Drawing Figures

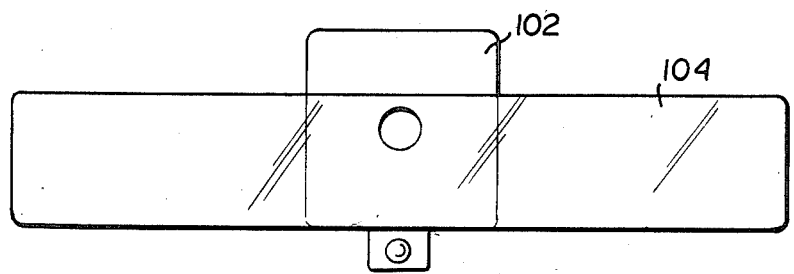
FIG. 13
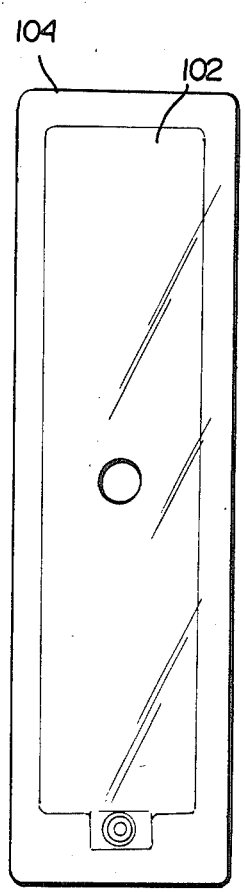
FIG. 12
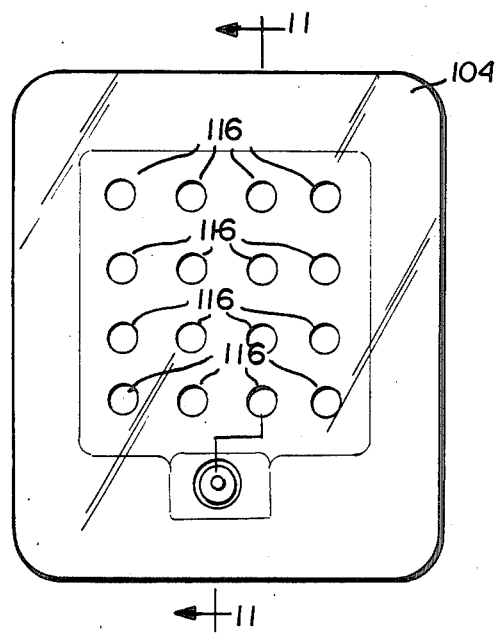
FIG. 10
FIG. 11
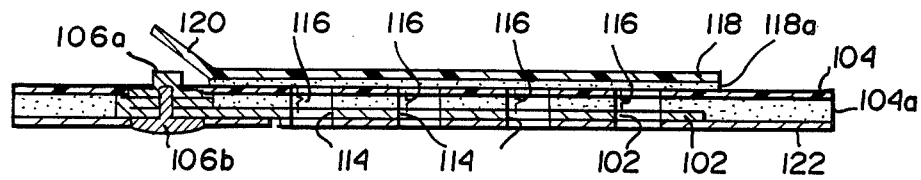

APERTURED ADHESIVELY APPLIED BODY ELECTRODE APPARATUS AND METHOD

This invention is generally directed to a body electrode for therapeutic and diagnostic applications in medical and veterinary use and to a method of establishing electrical contact with the external body surface of a living subject.

It is often necessary to establish a localized electrical contact with the external body surface of a living subject. Such contact is typically achieved by the use of electrically conductive electrodes having extended surface areas placed in electrical contact with a desired portion of an external body surface through an intermediate electrode gel, liquid or other preparation designed to ensure good and continuous electrical contact between the living body surface and the conductive electrode surface. Such electrical connections to living subjects are now commonly required for therapeutic and diagnostic applications in both medical and veterinary usage. For example, electro-therapeutic stimulation has now been recognized to promote the healing of bones and other body tissues and/or to have other advantageous physiological effects. Many diagnostic techniques (e.g., electrocardiograms) also require electrical connections to body surfaces so as to monitor electrical body surface potentials.

Prior body-electrode connection approaches have typically attempted to use a wide variety of conductive coatings, films, foils, plates or other elements. In general, such electrode surfaces have heretofore been held in place with wraps, adhesive tapes, adhesive films, adhesive gels, adhesive gums, and sometimes suction pressure.

Where contact is desired with a portion of the body that is not easy to wrap (e.g., the stifle of a horse), it may be necessary to rely upon adhesive affixation to the body surface. However, a rather common requirement for successful body electrode connections is the use of an electrode gel or other preparation to provide a conductive bridge between the electrode itself and the body skin or treatment site. The use of such electrode gels, liquids, or the like, unless specifically designed to have adhesive properties, are typically not compatible with adhesive tapes or other adhesive materials commonly used to hold the electrode in place. In fact, most electrode preparations serve as release agents for such adhesives. Accordingly, if the electrode preparation is applied in an area to which an adhesive connection is later desired, it may be then impossible to achieve the desired affixation.

Furthermore, this incompatibility between electrode gels (or other electrode preparations) and electrode adhesives becomes even more pronounced in the presence of body hair at the desired connection site. Thick hair or fur on animals, for example, will cause liquids and gels to naturally wick away from the desired application site and into surrounding areas where they subsequently will prevent the desired body adhesion from being established.

Conductive adhesive gels have experienced only limited effectiveness since they typically are adversely affected by body sweat which may cause slippage and even total loss of electrode contact with the body surface. Similarly, conductive adhesive gums (e.g., Karaya) are also affected by body sweat and are therefore commonly used only when direct contact can be made with dry skin. Furthermore, conductive adhesive gums do not easily flow through thick hair or fur and therefore cannot be practically used unless the treatment area is shaven. However, such shaving is often not practical (e.g., in the case of show or performance animals where shaven hair would draw undue attention to a possible defect or otherwise interfere with conformance ratings and animal value).

Now, however, I have discovered a new apertured adhesively applied electrode apparatus and method which advantageously avoids many of the abovementioned problems. This new arrangement is particularly suited for securing electrodes to treatment or measurement sites where electrode gels are required and where wrapping is not a practical matter or where the shaving of hair or fur from the treatment site is not desirable.

My new electrode is affixed to an external body surface prior to the application of electrode gels or other electrode preparations which may interfere with adhesion. In this way, the incompatibility with adhesives heretofore associated with pre-gelling or otherwise coating of the treatment site and/or electrode is avoided.

An adhesive-coated border around at least a portion of the electrode (and preferably completely thereabout) permits the electrode to be adhesively affixed to treatment locations where electrodes cannot easily be affixed by the traditional wrapping techniques. Such an adhesive border forms an occlusive seal with hair, fur and external body tissue surfaces at a time when the treatment site is still relatively clean and dry. Thereafter, the electrode gel or other preparation is inserted through at least one access aperture in the electrode structure. The soft, pliable and generally resilient external body surface of the subject, now disposed under such an aperture, permits a gel delivery nozzle or other suitable delivery device to penetrate through the hole to a reasonable depth of skin indentation as the required amount of gel or other preparation material is delivered into the interface area between the electrode surface and the intended body surface. If an array of plural apertures is distributed over the electrode surface, then the electrode gel or other electrode preparation may be manually applied and rubbed directly therethrough onto the subject body surfaces while the electrode is in place since normal wicking or other capillary-like actions will take such material beyond the aperture edges and into the desired interface area between the electrode surface and the intended body contact surface.

Thus, in brief summary, the exemplary embodiment of this invention provides a conductive patch with an adhesive boundary extending at least part way about the edges of that patch and with the patch having at least one aperture extending therethrough. The adhesive boundary may comprise a relatively larger adhesive-backed, flexible insulating sheet patch with a relatively smaller conductive patch being affixed therewithin (on the one adhesive-coated side). The insulating sheet has at least one aperture therein that is aligned with at least one aperture in the conductive patch area so as to collectively provide access aperture(s) to the treatment site. To facilitate storage, transport, etc., a release liner is also preferably included and is releasably attached to and covering the otherwise exposed adhesive-backing of the insulating sheet prior to its intended usage. Such a release liner typically is formed of two parts so that the flexible electrode assembly can be slightly flexed to permit easy fingertip access to an edge of the liner thus facilitating its easy removal just prior to the time of intended usage.

The exemplary embodiment also includes an adhesive-backed releasable cover member which is releasably attached to the non-adhesive coated side of the insulating sheet so as to cover the aperture(s) after the electrode gel or other preparation has been inserted into the interface region. Typically, such an adhesive-backed cover member will initially be in place covering the gel application aperture(s) and temporarily peeled away only during the gel insertion step. Thereafter, the adhesive-backed cover will be re-applied to close the aperture(s) and thus prevent unwanted leakage, evaporation or other loss of the electrode gel through the aperture(s).

An electrical snap-on connection terminal is preferably affixed to the conductive patch and extends backwards through a further aperture in the insulating sheet so as to permit ready electrical connection of a suitable electrical lead from an electrical signal generator or other conventional treatment/diagnostic apparatus. The conductive patch portion of the assembly is preferably flexible and may be formed from a thin metal foil patch pre-laminated to its own thin insulating coating so as to provide added structural strength and to facilitate adhesion to the adhesivebacked insulating patch.

These as well other objects and advantages of the invention will be better appreciated by carefully reading the following detailed description of the presently preferred exemplary embodiments of this invention taken in conjunction with the accompanying drawings, of which:

Figure 2:
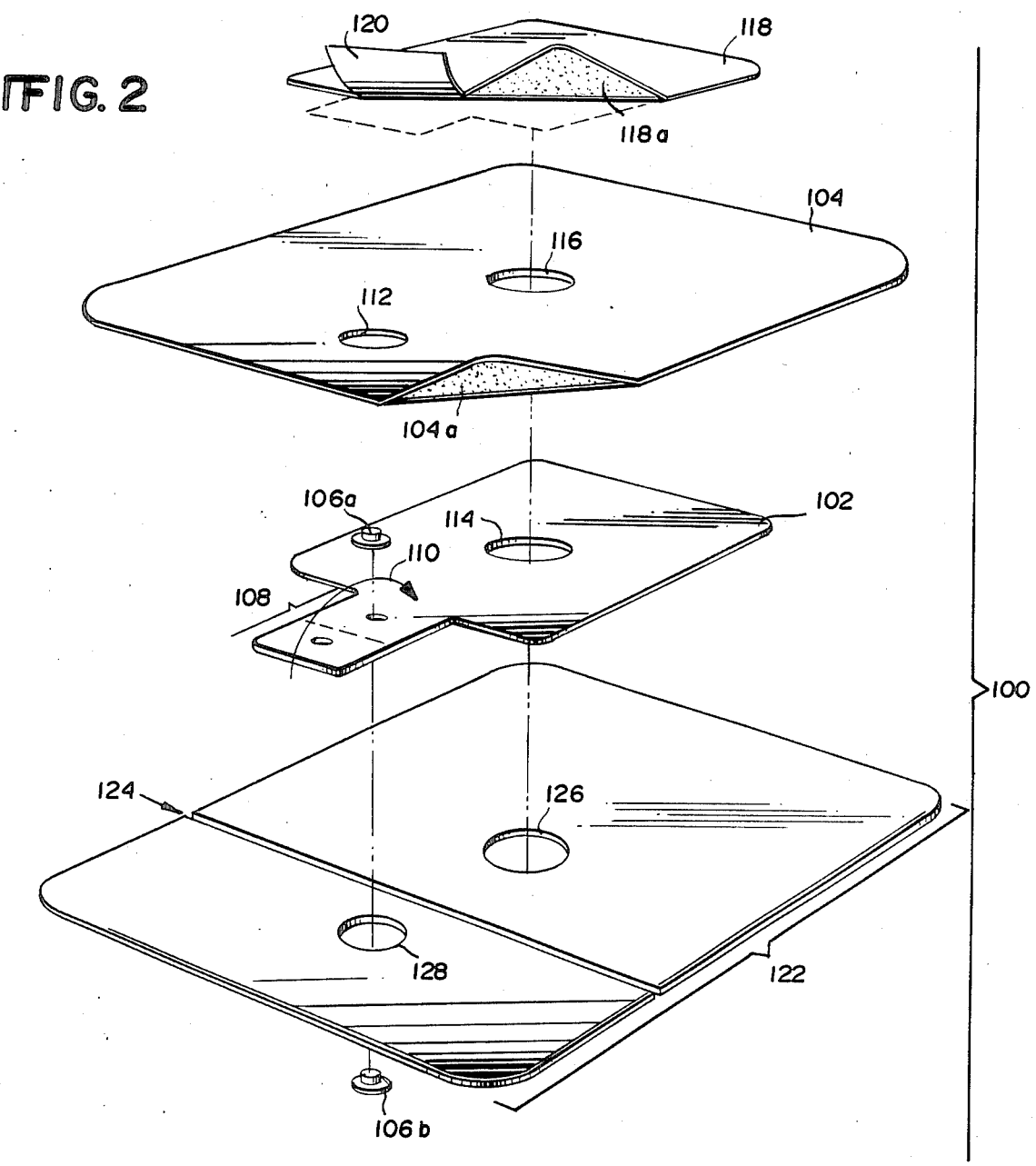
FIG. 2 is an exploded perspective view of the various components used in an exemplary embodiment of the adhesively applied electrode of this invention having a single aperture.

FIGS. 10 and 11 are a plan and cross-sectional view, respectively, of a second exemplary embodiment similar to that of FIG. 2 but having an array of plural apertures distributed thereover so as to facilitate a surface application of the electrode gel or other preparation rather than a pressurized nozzle delivery tube application or the like; and, FIGS. 12 and 13 are plan views of two further exemplary embodiments of the electrode structure.

Figure 1:
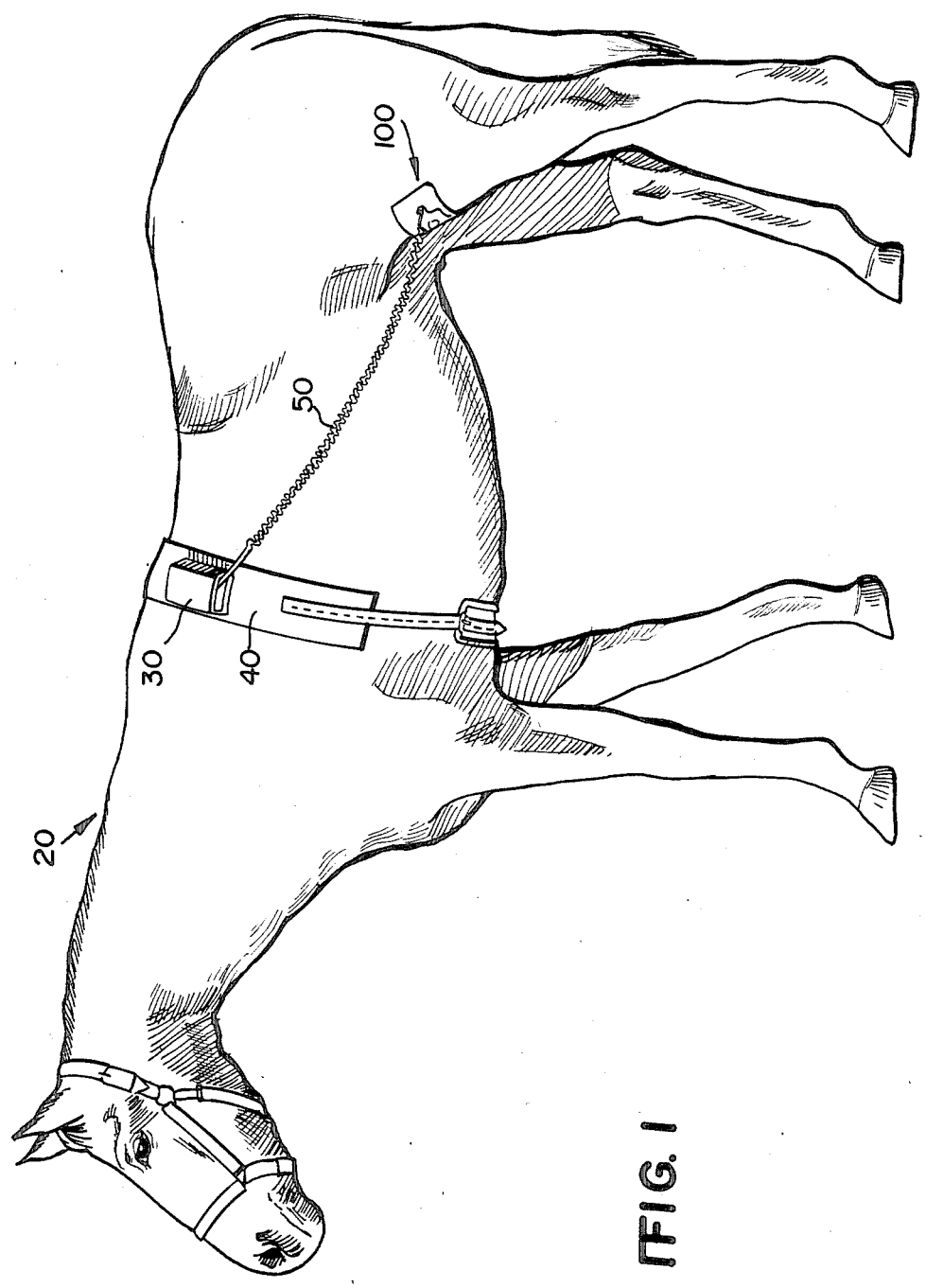
FIG. 1 is a general perspective view of this invention as used for therapeutic treatment of a horse.

FIG. 1 depicts a living subject 20 (e.g., a horse) having an external body surface to which electrical contact is desired at various sites to facilitate therapeutic treatment and/or diagnosis. For example, a bioelectric repair and maintenance stimulator 30 (e.g., an Ionicare unit, available from Murray Electronics, Veterinary Products Division, 260 Schilling Circle, Hunt Valley, Md. 21030) may be employed to treat an injury in the stifle area of horse 20. Typically, a surcingle electrode 40 of relatively large area is utilized as an anode while a relative smaller electrode 100 is applied near a desired treatment site (so as to provide an increased physiologically significant electrical current density thereabout) as a cathode electrode and connected to the signal source by lead wire 50. Repetitive-shaped electrical signal waveforms are then applied to the electrodes so as to achieve desired treatment effects.

The treatment electrode 100 is shown in FIG. 1 as being applied to the stifle area of a horse as being merely representative of one area in which it is difficult or perhaps even impossible to successfully secure an electrode by other more conventional wrapping means or the like.

Figure 3:
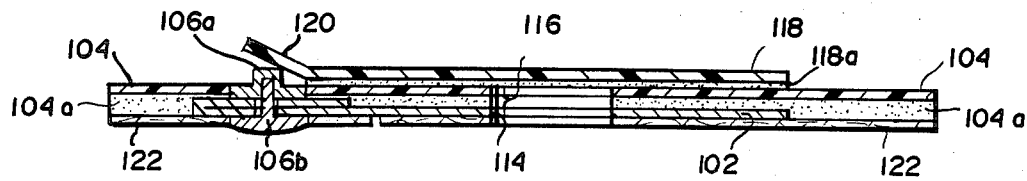
FIG. 3 is a cross-sectional view of the assembled electrode of FIG. 2.

Electrode 100 is shown in more detail at FIGS. 2 and 3. A conductive metal foil 102 constitutes the active electrode surface. In the exemplary embodiment, foil 102 is actually a very thin (e.g., 0.00035 inch) layer of aluminum foil pre-laminated to a very thin (e.g., 0.00092 inch) layer of polyester film (laminated to the top of structure 102 as seen in FIG. 2) so as to provide added structural strength and to facilitate adhesive affixation within the central portion of a larger flexible insulating sheet 104 (having an adhesive coating 104a on its lower surface as seen in FIG. 2). The laminated aluminum foil/polyester film 102 may be cut from commercially available material (e.g. part No. 1035 from Lam-A-Shield Incorporated, Cleveland, Ohio). The presently preferred adhesivebacked patch 104 also cut from commercially available material (e.g. part No. 7350 from 3M Corporation which comprises a thin (e.g., 0.002 inch) insulating sheet of polypropylene with a thin (e.g., 0.0008 inch) coating of acrylic adhesive 104 on one side).

A conventional snap-on type electrical connector comprising mated parts 106a and 106b is attached to a folded-over tab portion 108 of the laminated aluminum foil structure 102. Since it is folded over (as indicated by arrow 110), a conductive aluminum foil surface is exposed on both the top and bottom of the thus double thickness tab portion 108 for increased structural support and electrical area connection with the snap-on devices 106a, 106b. The snap-on connector part 106a has a connector projection which extends backwardly (i.e. upwardly in FIG. 2) through an aperture 112 in the insulating patch 104 so as to be readily available for snap-on electrical connection to lead wire 50 (as shown in FIG. 1).

As shown in FIG. 2, the conductive patch 102 includes an aperture 114 which is aligned with a similar aperture 116 in the overlying insulating patch 104 so as to permit the insertion therethrough of electrode gel or other preparations (as will be described in more detail below). A controllable (i.e. releasable) aperture closure 118 is formed by another adhesive-backed layer (e.g., of material the same as or similar to the material of insulating sheet 104) including adhesive 1182. The closure 118 may include a non-adhesive finger access tab 120 to facilitate its controlled removal from closure position when it is desired to insert electrode gel or the like through apertures 116, 114 and to thereafter be re-applied to close these apertures and thus prevent undesirable loss of electrode gel or other preparation after it is in place.

The flexible electrode assembly of FIGS. 2–3 also includes a releasable liner layer 122 which is normally in place covering the otherwise exposed portions of the adhesive surface 104a until the intended time of usage. Typically, the release liner 122 will include a break 124 so that the entire assembly may be slightly bent at the break to gain finger access to a free edge of the releasable liner 122 and thus facilitate its strippage from the adhesive layer 104a and ready the assembly for adhesive affixation to the desired body surface area.

Release liner 122 is shown as including apertures 126, 128. Aperture 128 typically occurs because the liner 122 already may be in place when apertures 114 and 116 are cut during manufacturing processes and aperture 128 permits the assembly of snap-on connector 106a, 106b while the release liner 122 remains in place thus protecting the adhesive layer 104a during manufacturing processes. However it will be appreciated that such apertures are not required since the release liner 122 is typically removed before the remainder of the electrode assembly shown in FIGS. 2-3 is adhesively affixed to a desired body surface site and used.

Figure 4:
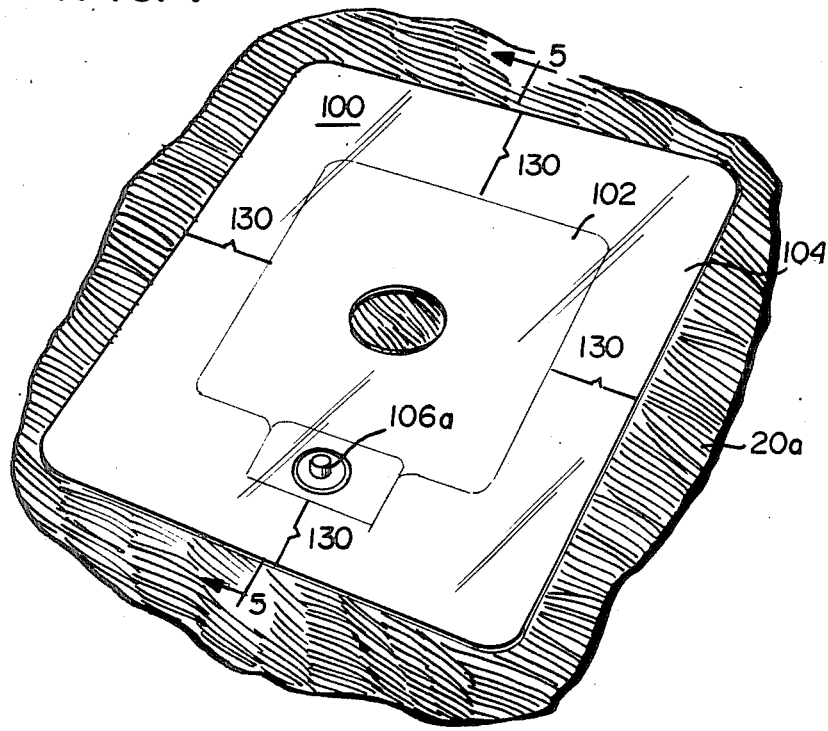
FIGS. 4–9 are perspective and cross-sectional views of the FIG. 2 embodiment in place with the external body surface of a living subject and successively illustrate a method of establishing electrical contact therewith using the electrode embodiment of FIG. 2.
Figure 5:
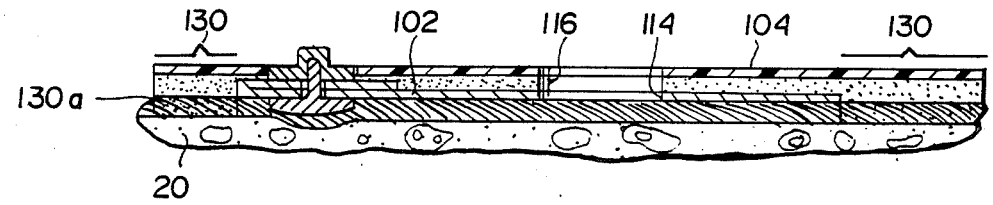
Figure 6:
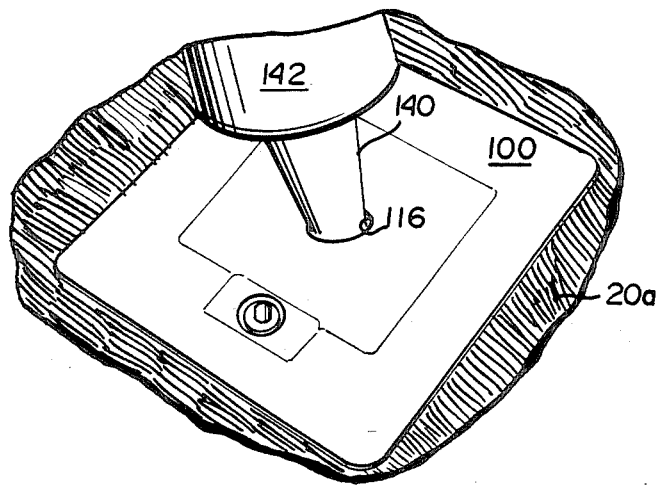
Figure 7:
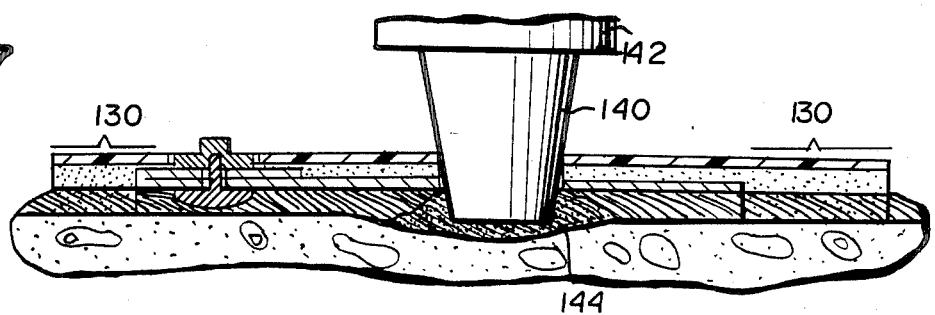

FIG. 4 depicts the electrode 100 of FIGS. 2-3 with the releasable liner 122 removed and the remainder of the assembly adhesively secured in place to a desired external body surface 20a of a living subject. Typically, the treatment site 20a should be clean and dry and the connector end of cable 50 may be snapped onto the snap connector 106a prior to installation of the electrode patch 100 onto the treatment site. Once the protective releasable liner 122 has been removed so as to expose a boundary 130 of adhesive 104a (extending all about the centrally located conductive patch 102 in the exemplary embodiment), the assembly may be positioned as desired over site 20a and pressed firmly thereto so as to assure a good adhesive bond. As shown in the cross-sectional view of FIG. 5, the boundary areas 130 will include an adhesively sealed and occluded area 130a which incorporates any contiguous body hair (or fur) so as to provide a substantially impervious seal between the external surface of living body 20 and the periphery of the conductive electrode 102.

Figure 8:
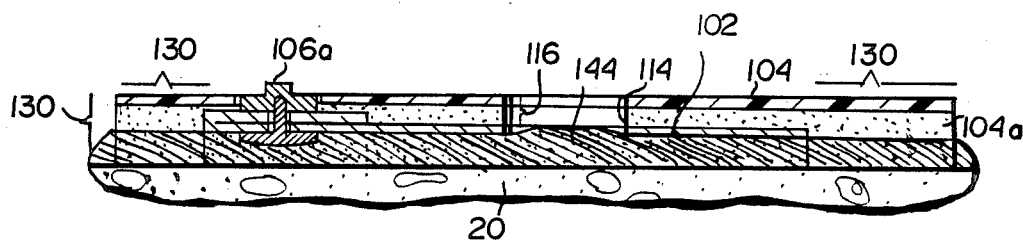
Figure 9:
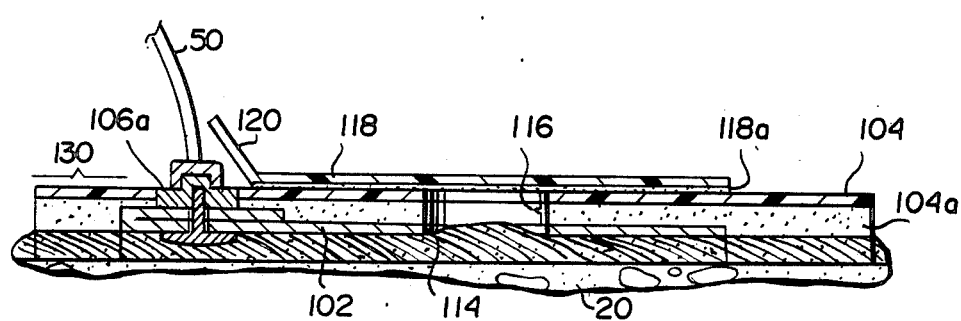

As shown in FIGS. 4-8, the controllable closure layer 118 has already been removed so as to permit the insertion of a nozzle 140 (or other suitable applicator) of a container 142 of conventional electrode gel or other preparation. The external surface of body 20 is typically sufficiently pliable and resilient to permit the end of nozzle 140 and the extruded gel 144 (e.g., extruded when hand pressure is applied to collapsible container 142) so as to slightly depress the external skin and permit the electrode gel to flow into and fill the interface volume between the aluminum foil conductive surface of the conductive patch 102 and the external skin surface of body 20. FIG. 8 depicts such a filled condition while FIG. 9 depicts the replacement of closure 118 so as to prevent undesirable loss of gel thereafter through the aperture.

When the electrode structure is to be used on horses, it has been experimentally determined that the border area 130 of adhesive available for affixation should probably be at least about 0.75 inch wide to insure good adhesive affixation. Preferably, such adhesive is provided in a substantially continuous border 130 all about the conductive patch 102. However, as should be appreciated, for some applications it may not be necessary to have such a continuous enclosure of the electrode/gel/-skin interface. FIG. 13, for example, depicts an alternate embodiment without such a continuous adhesive border.

The embodiment of FIGS. 10 and 11 is similar to that of FIGS. 2 and 3 except that there is now an array of plural apertures 116, 114 through the insulating patch 104 and conductive patch 102. Accordingly, similar reference numerals are used in FIGS. 10 and 11 to depict similar parts. The use of plural apertures facilitates the surface application (e.g., by rubbing a saturated cloth or the like) of electrode gel or other preparations through the exposed apertures. Wicking or other capillary-like forces (possibly including manual massage of the surface of the patch) will result in substantially uniform and continuous filling of the interface volume between the conductive electrode patch and the skin surface.

After the electrode is adhesively affixed in place, but before the electrode gel or other preparation is inserted through apertures 116, 114, it may be desirable to apply a small quantity of water through such aperture(s) so as to pre-moisten the hairs or surface coat of the treatment site. Thereafter, the electrode gel or other preparation can be inserted into the interface volume until the surface of the flexible electrode bulges slightly (i.e., in the FIGS. 2-3 embodiment where the electrode gel is extruded into the interface volume through a single aperture and under pressure). The surface of the flexible electrode assembly may thereafter be massaged manually so as to better work the electrode gel into the hair or other surface coat of the skin at the treatment site. As will be appreciated, the external surface of the layer 104 may be cleaned of any excess electrode preparation before the aperture closure 118 is re-affixed.

As should be appreciated, other patch shapes may utilize the principles of this invention and, for example, an elongated rectangular patch is depicted in FIG. 12. Similarly, as earlier mentioned, for some applications it may not be necessary or even desirable to have a completely continuous adhesive border about the conductive patch 102. Accordingly, in such cases, the adhesive-backed flexible insulating patch 104 may have a considerably different shape from that of the conductive patch 102 as is, for example, depicted at FIG. 13. It will also be appreciated that the adhesive backing might in some cases be applied directly to the periphery or other desired portions of the conductive electrode structure itself. The conductive patch may also be formed by printing, painting or otherwise placing conductive ink on a suitable substrate. However, in the present exemplary embodiments, aluminum foil is preferred (e.g., it is conceivable that the ions which make an ink conductive might, over time, migrate under influence of the electrical treatment fields away from the printed ink itself thus deteriorating the overall electrode function).

Although the exemplary embodiments have been described with respect to veterinarian usage on animals such as horses, it will be understood that the same electrode apparatus and method may also be utilized to achieve conductive coupling to the external skin surfaces of human subjects as well.

In the present exemplary embodiment, the conductive patch 102 may be approximately 3 inches square (exclusive of tab 108) while the insulating patch 104 may be approximately $5 \times 5\frac{1}{2}$ inches in overall dimension. Apertures 114, 116 in the embodiment of FIGS. 2-3 may be approximately 0.688 inch diameter while the individual apertures in the embodiment of FIGS. 10-11 may each be of approximately 0.31 inch diameter.

Although this invention has been above-described only with respect to a few presently preferred exemplary embodiments, those skilled in the art will recognize that many variations and modifications may be made in these embodiments while yet retaining many of the novel features and advantages of this invention. The following claims are intended to cover all such variations and modifications.

What is claimed is:

1. A flexible electrode for therapeutic or diagnostic applications which may be adhesively affixed to the external body surface of a subject prior to the application of electrically conductive electrode preparations between the body surface and the flexible electrode, said flexible electrode comprising:

a conductive patch having a substantially flat body-engaging flexible conductive foil surface for engagement with the body surface and which is in a flexible sheet form;

an electrical terminal affixed to said conductive patch and adapted for connection to an electrical lead;

a flexible insulating sheet having lateral dimensions in excess of the corresponding lateral dimensions of said conductive patch and having an adhesive covering on one side thereof, said conductive patch being affixed thereto on said one adhesive side;

the margins of said sheet, said adhesive on said one side and said conductive patch defining an adhesive boundary about said electrode for adhesive affixation of said flexible conductive surface to the body surface in a taut extended condition;

each of said flexible conductive foil and said sheet having at least one aperture extending completely therethrough and aligned one with the other for providing open access through the entire flexible electrode to the body surface after adhesive affixation thereto to enable application of the electrically conductive electrode preparation through the aligned apertures into the area between the body surface and the said body engaging flexible conductive surface; and a release liner releasably attached to and covering the otherwise remaining exposed adhesive backing of said sheet defining said boundary and the otherwise exposed side of said conductive patch prior to its intended use.

2. An electrode as in claim 1 further comprising an adhesive-backed releasable cover member releasably attached to the other side of said sheet and covering said aligned apertures.

3. An electrode as in claim 1 wherein said conductive patch comprises a metal foil patch pre-laminated with an insulating coating on the side affixed to said sheet and having a doubled-back tab area at which said terminal is affixed with electrical connections being effected to both the exposed top and bottom metal foil surfaces in the thus double thickness tab area.

4. An electrode as in claim 1 wherein said conductive patch includes an array of plural apertures distributed thereover.

5. An electrode as in claim 4 wherein said conductive patch and said sheet include an array of plural aligned apertures.

* * * * *